(12) United States Patent
Kiehne

(10) Patent No.: US 7,857,824 B2
(45) Date of Patent: Dec. 28, 2010

(54) SURGICAL SCALPEL WITH RETRACTABLE GUARD

(75) Inventor: Bruce Leigh Kiehne, Springwood (AU)

(73) Assignee: Southmedic Inc., Barrie, Ontario (CA)

( * ) Notice: Subject to any disclaimer, the term of this patent is extended or adjusted under 35 U.S.C. 154(b) by 588 days.

(21) Appl. No.: 10/528,422

(22) PCT Filed: Sep. 10, 2003

(86) PCT No.: PCT/AU03/01187

§ 371 (c)(1),
(2), (4) Date: Sep. 21, 2005

(87) PCT Pub. No.: WO2004/026151

PCT Pub. Date: Apr. 1, 2004

(65) Prior Publication Data

US 2006/0100650 A1 May 11, 2006

(30) Foreign Application Priority Data

Sep. 20, 2002 (AU) ............................. 2002951534
Jul. 22, 2003 (AU) ............................. 2003903812

(51) Int. Cl.
*A61B 17/32* (2006.01)
(52) U.S. Cl. ............................. 606/167; 30/151; 30/162
(58) Field of Classification Search ................ 606/167, 606/170, 181; 30/162, 151
See application file for complete search history.

(56) References Cited

U.S. PATENT DOCUMENTS

| 3,905,101 | A |   | 9/1975 | Shepherd |
| 5,868,771 | A |   | 2/1999 | Herbert et al. |
| 6,058,607 | A | * | 5/2000 | Gringer ................ 30/162 |

FOREIGN PATENT DOCUMENTS

| EP | 555196 |    | 8/1993 |
| EP | 555196 A1 | * | 8/1993 |
| JP | 55-48439 |    | 9/1953 |
| WO | WO 01/05312 |   | 1/2001 |
| WO | WO 01/05312 A1 | * | 1/2001 |
| WO | WO 01/74257 |   | 10/2001 |

* cited by examiner

*Primary Examiner*—Anhtuan T Nguyen
*Assistant Examiner*—Julie A Szpira
(74) *Attorney, Agent, or Firm*—Stein McEwen, LLP

(57) ABSTRACT

A safety scalpel blade assembly adapted for attachment to a handle (12), the assembly comprising a scalpel blade (10) and guard (11) which extends at least about the cutting edge of the blade (10), the guard (11) having attachment means to lock the blade to the guard as the assembly is being attached to the handle and which releases the blade from the guard when the blade is attached to the blade carrier on the handle. Improvements include a removable safety tab (60) on the guard (11), means (68,71) to prevent the blade guard (11) lifting relative to the handle (12), a safely catch (75) to prevent excessive retraction of the guard (11) and location means (80,82) to locate the guard (11) in the extended and retracted positions.

14 Claims, 16 Drawing Sheets

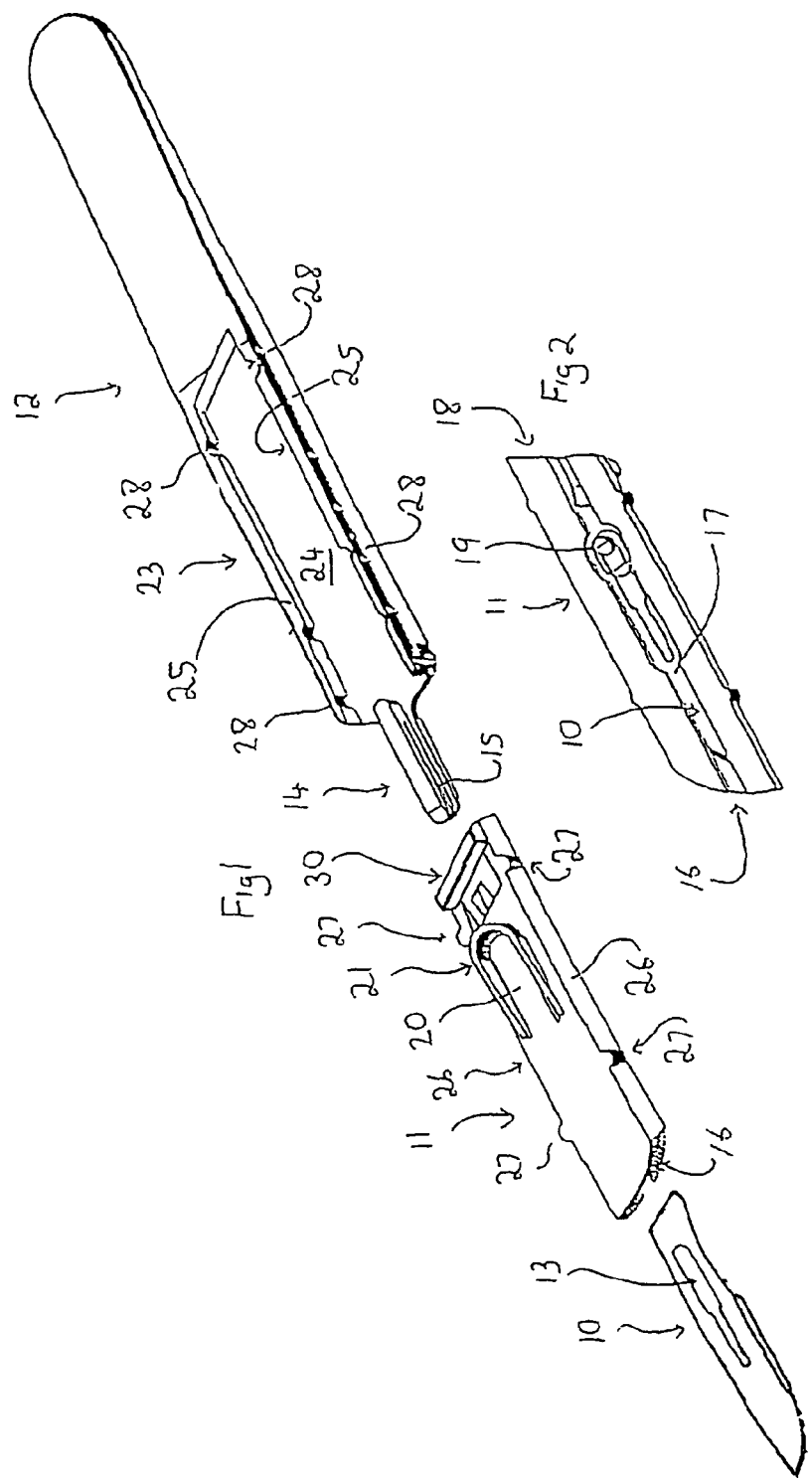

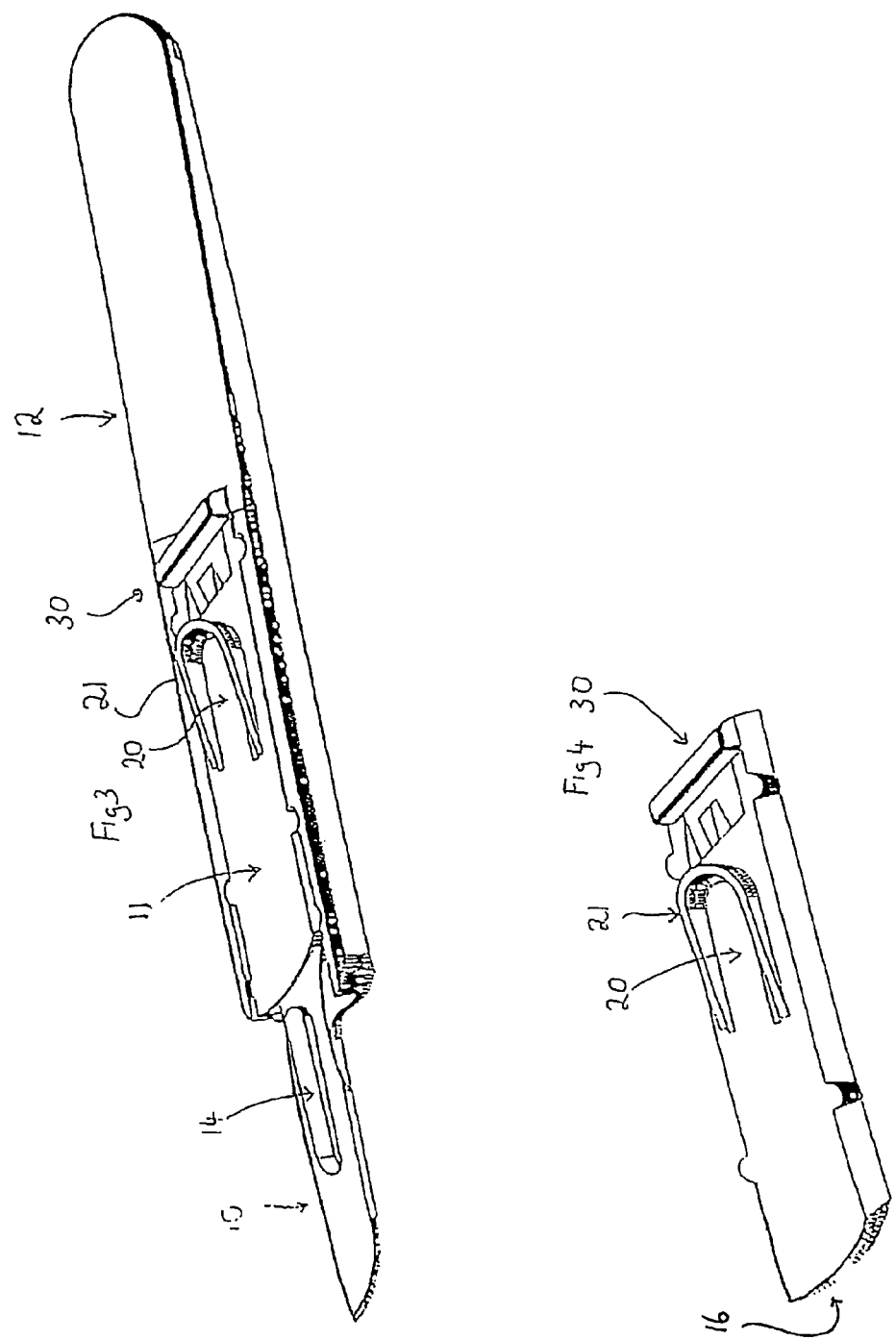

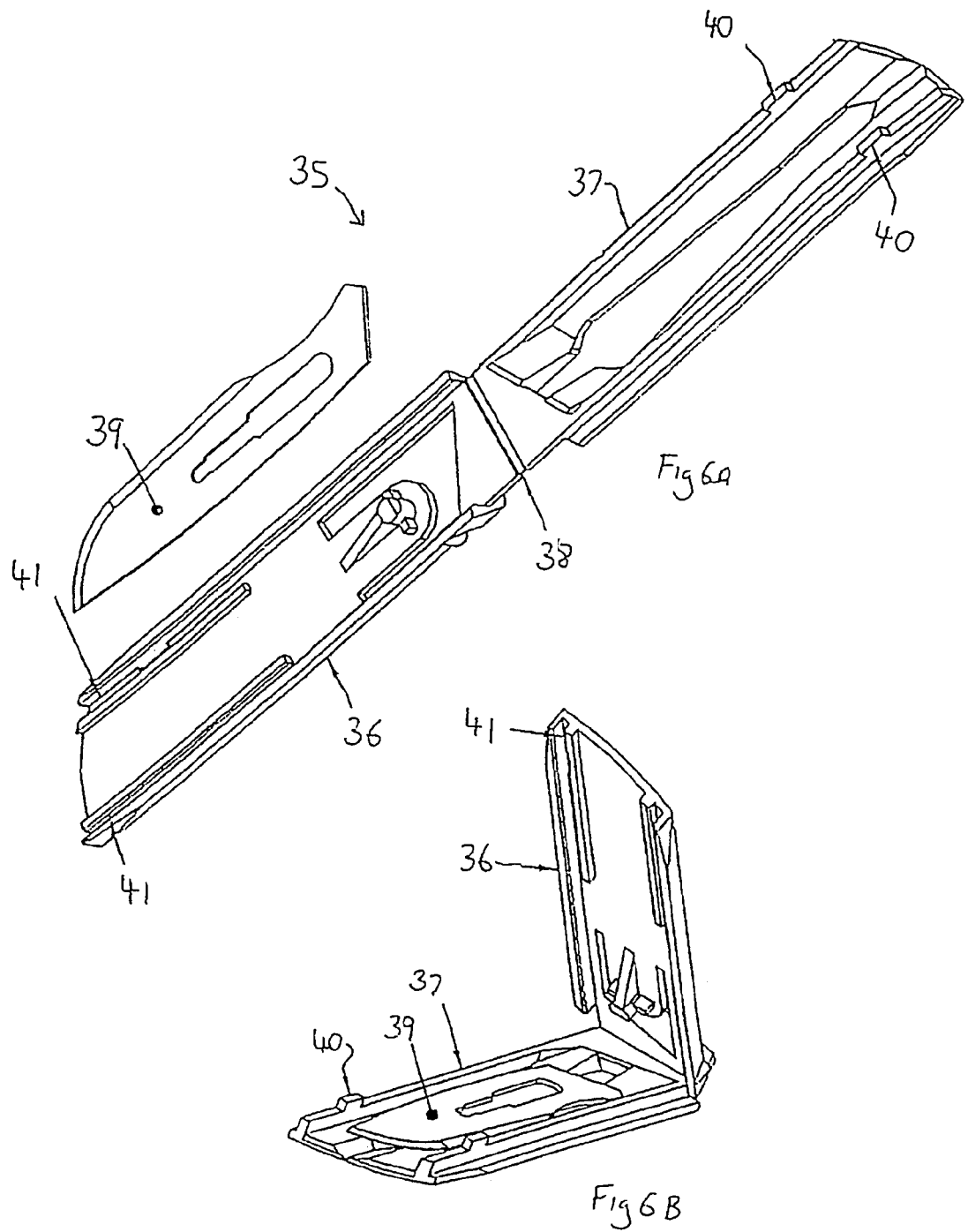

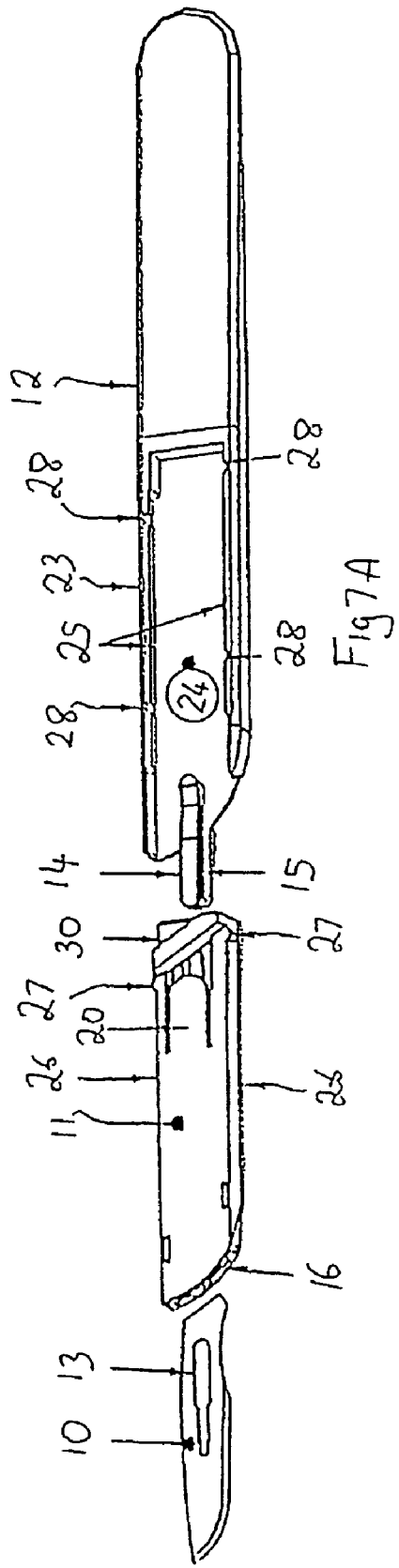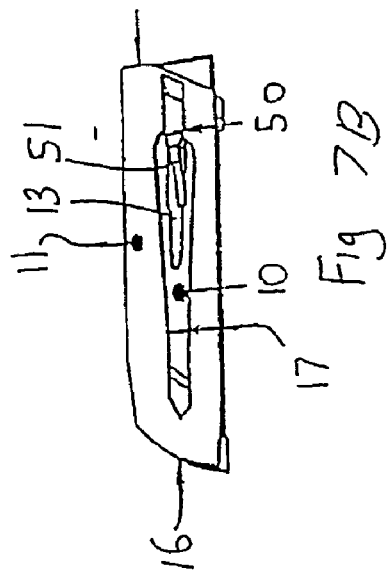

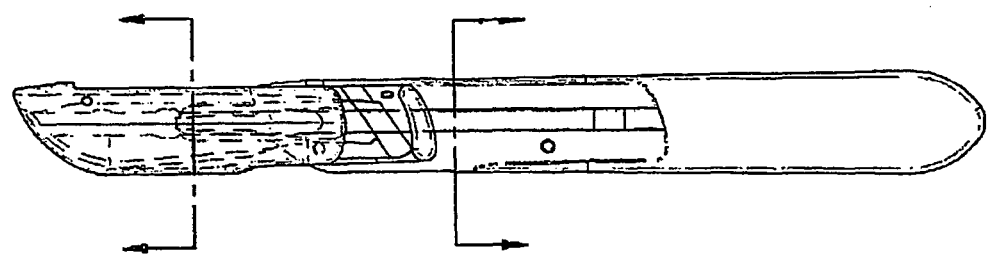
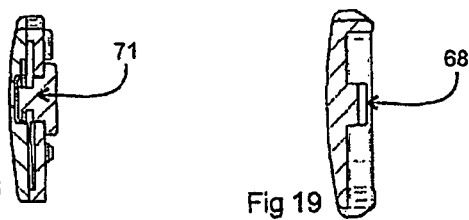
Fig 18  Fig 19
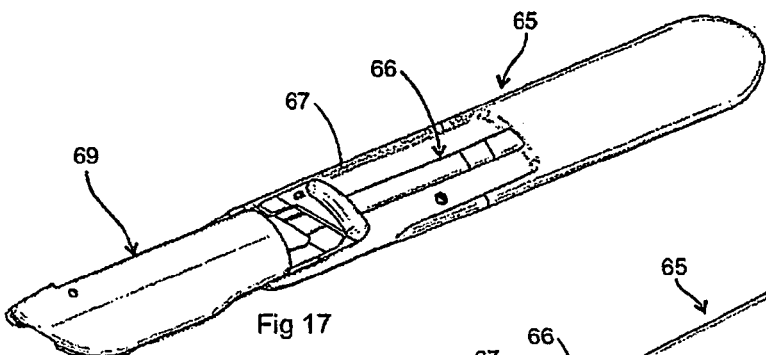
Fig 17
Fig 16
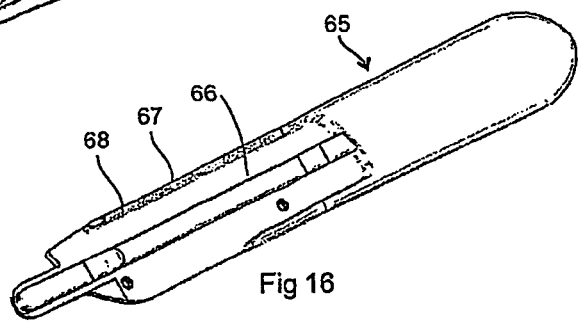
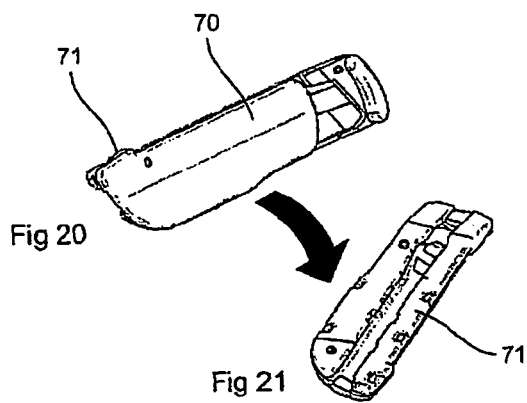
Fig 20
Fig 21

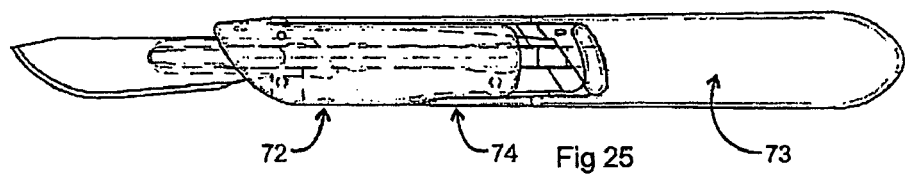
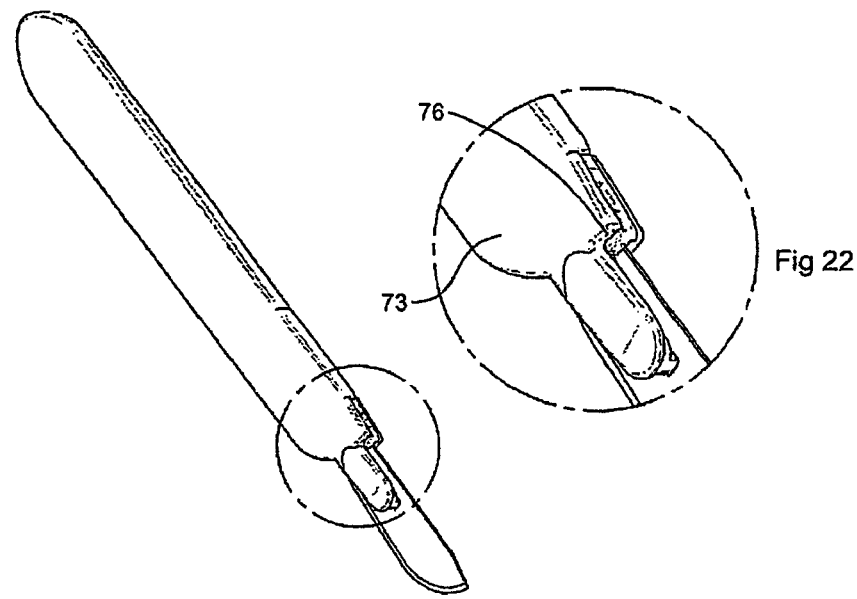
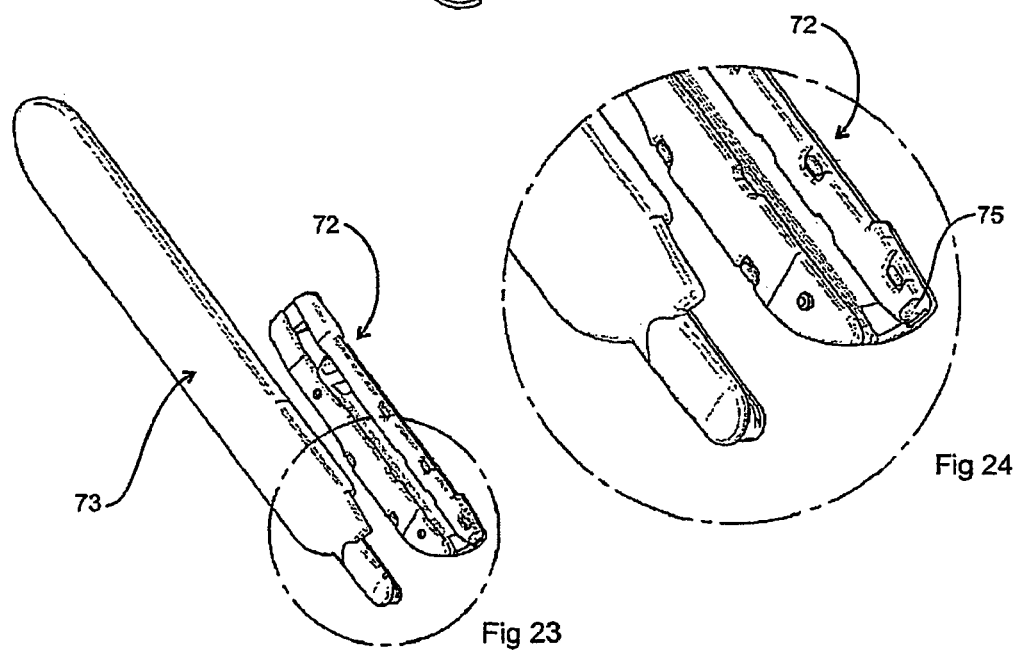

SURGICAL SCALPEL WITH RETRACTABLE GUARD

FIELD OF THE INVENTION

This invention relates to various improvements to a surgical scalpel which has a retractable guard to reduce the incidence of sharps injury.

The invention will be described with reference to a surgical scalpel but it should be appreciated that the invention can be construed broadly enough to cover any other type of cutting implement which requires safe handling procedures.

BACKGROUND ART

Surgical scalpels or surgical knives which are in commercial use have a handle and a disposable blade. The blade can be detached from the handle and disposed of by deposit in a special container which can thereafter be handled with reduced hazard of sharps injury.

A sharps injury means any cutting or penetrating object that can be reasonably anticipated to penetrate the skin or other part of the body to result in an exposure incident which includes occupational exposure to blood and other potentially infectious materials. Clearly, this covers scalpels and other types of surgical knives.

The commercially available scalpels which have a disposable blade generally have reusable handles. The handle can be sterilised by autoclaving and reused, and these handles are usually formed from metal.

The surgical blade comes packaged in a protective foil. The foil is carefully opened to expose the blade. The blade is then held between thumb and finger and carefully attached to an extending projection of finger on the handle. Upon completion of the surgical procedure, the blade is either manually detached from the handle and placed in a sharps bin, or the handle with the blade is inserted into a container which breaks off the blade.

It can be seen that attachment of the blade to the handle is a hazardous procedure and can easily result in a sharps injury. If the blade is manually detached, this can also result in a sharps injury which is even more hazardous as the blade may be contaminated.

During surgical use, the scalpels can accidentally cut the surgeon's fingers, or the fingers of nurses and other support persons in the operating theatre. As well, operating personnel can be accidentally cut when the scalpel is passed between personnel.

To partially mitigate against accidental sharps injuries in handling the scalpel, it is known to provide a retractable blade guard. The blade guard is attached to the handle, and can be manually pushed between an extended blade guarding position, and a retracted blade exposed position Thus, blade guards attached to scalpel handles are known.

These blade guards have some disadvantages. Firstly, by being part of the handle, the handle must be thoroughly cleaned from any blood and tissue after use, if the handle is to be reused. The blade guard can catch and contain tissue, congealed blood, and the like in the various nooks and cavities in the blade guard and it is extremely difficult to ensure that the blade guard is absolutely spotlessly clean to allow the handle with the attached blade guard to be reused. To allow the handle to be reused many times, the blade guard must be fairly robust and this can result in the guard being of fairly complex manufacture, quite bulky, and quite expensive.

A second disadvantage with this arrangement is that the blade guard cannot protect against initial attachment of the sterile blade to the handle. That is, the blade guard must be fully retracted to expose the projection or finger on the handle to which the blade is attached. The blade must be attached in the usual manner which is to initially remove it from its protective foil and then physically attach it to the handle. Thus, existing blade guards do not reduce or eliminate sharps injuries which can result in initial attachment of the blade. As well, these guards do not protect against removal of the blade from the handle.

Our earlier international patent application WO 01/05312 described a surgical scalpel with a retractable guard. The device overcame many of the above-mentioned disadvantages.

However, attachment of the blade to the handle could still risk a sharps injury especially if the person attaching the blade was inattentive or very junior.

With larger blades and handles there was the possibility that the guard could "pop off" the handle when retracted due to some flexibility in the larger guard.

It was also possible to pull the guard back too far and to pull the guard off the handle.

When the guard was retracted to expose the blade and extended to cover the blade, there was the possibility of insufficient retraction and extension which could cause a portion of the blade to be exposed [with insufficient extension] or only partial exposure of the blade cutting edge [with insufficient retraction]. It was also possible for the guard to inadvertently move during use. Thus a visual check was needed. However there would be an advantage if the fully retracted position and the fully extended position could be sensed without constant visual checking, and/or if these positions could be lightly "locked" in place.

OBJECT OF THE INVENTION

The present invention is directed to improvements with respect to a surgical scalpel with a retractable guard, and particularly to improvements in respect of the device described in our earlier international patent application.

The present invention is directed to improvements to a guard assembly which contains a blade attached to a blade guard. The assembly can be packaged within a sterile foil (similar to conventional blades). The assembly can be removed from the foil and can be safely handled with little risk of the blade cutting the person, and the assembly can be attached to a scalpel handle with the blade guard in place.

When the assembly is attached to the scalpel handle, the blade guard can be retracted fully or partially to expose the blade. When the surgical procedure is finished, the blade guard can be pushed back over the blade and the blade and blade guard can be removed from the handle for safe disposal. In this arrangement, the handle itself does not keep the blade guard as the guard is disposed with the blade after use.

With this arrangement, there is reduced likelihood of sharps injuries in attachment of a blade to the handle. As well, the handle does not keep the guard which means that the handle can be more easily cleaned and sterilized for reuse. The guard can stay with the blade when the blade is removed which reduces the incidence of sharps injury when removing the blade from the handle.

In one form, the invention resides in a means to improve the method of attachment of the blade assembly to a handle.

In this form, the invention comprises the provision of a removable tab on the blade assembly which can be removed after the blade has been attached to the handle and prior to exposing the blade by retracting the guard.

Thus, one form of this invention comprises a safety scalpel blade assembly adapted for attachment to a handle of the type which has a blade carrier in the form of a finger, the assembly comprising a scalpel blade which can be of conventional manufacture, the scalpel blade having a slot to allow the blade to be attached to the blade carrier on the handle, and a guard which extends at least about the cutting edge of the blade, the guard having attachment means to lock the blade to the guard as the assembly is being attached to the handle and which releases the blade from the guard when the blade is attached to the blade carrier on the handle, and a removable tab on the guard having a portion which can be gripped by a person.

Suitably, the removable tab has a head portion and a tail portion. The head portion suitably extends forwardly of the blade assembly. The tail portion suitably extends at least partially into a slot which is present in the guard.

Suitably, the removable tab is attached to the guard via at least one breakable portion. Suitably, a plurality of breakable portions are provided. These breakable portions are preferably on the tail portion of the removable tab.

Suitably, the breakable portions comprise a first breakable portion (a first neck) and a second breakable portion (a second neck). It is preferred that the first breakable portion is closer to the head portion of the removable tab and can break more easily than the second breakable portion. Thus, the first breakable portion may be sized for immediate breakage. The second breakable portion may be more difficult to break and may require both a twisting action and a leveraged action against the underside of the blade to break to ensure that the head of the safety tab has moved sufficiently away from the blade exposure to be safely operated by hand.

Thus the function of the tab can be to initially prevent retraction of the guard and exposure of the blade, until the tab is removed after which the guard can be retracted and the blade exposed. Thus the tab provides an improvement to the invention by preventing inadvertent or premature exposure of the blade.

The head portion of the removable tab can either be gripped by a person or may be placed against a solid surface and pushed, both options allowing the tab to be removed and allowing the guard to be attached to the handle with a reduced likelihood of being cut by the blade.

In another form the invention resides in an improvement to a surgical scalpel with a retractable guard and which contains a blade assembly, the blade assembly comprising a blade and a blade guard, the improvement comprising means to reduce the ability of the blade guard from lifting relative to the handle.

This improvement overcomes a disadvantage with earlier devices and especially earlier devices which comprise a larger handle and a relatively large guard. The disadvantage was that is the guard had a degree of flexibility and could inadvertently be removed from the handle thereby presenting a sharps hazard situation.

In one form, the means can comprise an engagement means on the handle and which engages the guard. The engagement means may comprise an elongated rib or rail in the handle, and a corresponding groove or slot in the guard (or vice versa) such that the guard can slide between the forward and the retracted position but is held against being lifted by the engagement of the rib or rail in the groove or slot. Of course, other means to prevent the guard from being lifted relative to the handle are envisaged.

Another means to prevent the guard from being inadvertently removed may comprise a means to prevent the guard from being retracted too far thereby creating the possibility that the guard can be pushed out of engagement with the handle.

In one form, this means may comprise an engagement means such as a safety catch which prevents excessive retraction of the guard. The safety catch may be provided on the guard can preferably on a forward portion of the guard. The safety catch may comprise a peg or similar type of member.

Another improvement to the scalpel with retractable guard comprises a means to positively locate the guard in the extended position and the retracted position. The means may comprise at least one projection which can releasably engage in at least one recess when the guard is in the extended position and the retracted position. The arrangement may be such that an audible "click" is heard when the guard is in the extended position or the retracted position, or that a tactile response is felt.

In each improvement, the scalpel blade assembly may be of the type described in our earlier international patent application and may comprise a scalpel blade assembly comprising a scalpel blade, a guard which extends at least about the cutting edge of the blade, and releasable attachment means to releasably attach the blade to the guard, the attachment means being operable between a locking position where the blade is held relative to the guard such that the cutting edge is protected by the guard, and a free position where the blade can slide out of the guard.

In a more particularised form, the safety scalpel blade assembly which is able to be attached to a handle of the type comprises a blade carrier in the form of a finger, the assembly comprising a scalpel blade which can be of conventional manufacture and which has a slot which allows the blade to be attached to the blade carrier on the handle, and a guard which extends at least about the cutting edge of the blade, the guard having attachment means which locks the blade to the guard as the assembly is being attached to the handle thereby preventing the blade from cutting a person, but which releases the blade from the guard when the blade is attached to the blade carrier on the handle.

In another form, the invention resides in improvements to a scalpel comprising a scalpel blade assembly and a handle, the scalpel blade assembly having: a scalpel blade, a guard which extends at least about the cutting edge of the blade, and releasable attachment means to releasably attach the blade to the guard, the attachment means being operable between a locking position where the blade is held relative to the guard such that the cutting edge is protected by the guard, and a free position where the blade can slide out of the guard, the handle having:

a portion which is releasably lockable to the blade, the handle further having guide means which engages with the guard when the handle is attached to the blade to allow the guard to slide along the guide means on the handle between a retracted position where at least a portion of the cutting edge of the blade is exposed, and an extended position where the cutting edge of the blade is protected, the scalpel further having means to move the attachment means to its free position when the handle is attached to the blade, and at least one improvement as described above.

The scalpel blade assembly has the scalpel blade initially attached to a blade guard. The assembly can be packed in a sterile foil and the foil can be opened to safely remove the blade and the blade guard. The assembly can then be attached to a scalpel handle and thereafter the guard can be retracted to-expose the scalpel blade.

The scalpel blade can be of various types depending on the surgical procedure to be carried out. It is usual for the blade to be elongate and to have a forward cutting edge. The blade body is provided with an elongate slot extending therethrough and the slot allows the blade to be attached to a projection or finger on the handle. This arrangement is entirely conventional. The invention is envisaged to cover surgical devices which may be other than a blade but which also are attachable to a handle and which require safe handling procedures.

The guard extends at least about the cutting edge of the blade to protect against sharps injury. The guard may be formed from plastics material although other materials are envisaged. As the blade assembly is disposed of after use, it is preferred that the guard is made of fairly inexpensive material which is however still suited for use and which can be sterilised.

The guard can extend substantially around the blade to form a shroud or sleeve. The forward end of the guard (that is the end where the front of the blade sits) should be open or have a passageway to allow the blade to extend from the guard. To facilitate attachment of the blade/guard assembly to the handle, the guard may be required to have an opening or slot to allow the handle to be attached to the blade while the guard is still in place, and to allow the guard to be retracted from the blade when the blade is attached to the handle.

The assembly has a releasable attachment means. The releasable attachment means functions to initially attach the blade to the guard such that when the blade/guard assembly is removed from its protective package, the blade does not inadvertently fall out of the guard or expose a cutting edge. The attachment means can also function to hold the blade in the guard when the blade is removed for disposal. In one form, this can be achieved by a projection or button on the guard which extends into the slot in the blade body (the slot being where the handle attaches to the blade).

The projection or button therefore prevents the blade from inadvertently sliding out of the guard and presenting a cutting edge.

If desired, the guard may be provided with a further projection, or fin which extends into the slot in the blade and can function to prevent the blade from "rattling" in the guard.

The releasable attachment means may also be slightly biased, inter alia to push the blade against a wall of the guard again to prevent the blade from rattling or exhibiting undesired movement in the guard.

The blade assembly can be attached to a scalpel or knife handle. The knife handle can have a forward projection or finger which has a profile to allow it to releasably lock to the slot in the blade. This arrangement is known in the art. The handle can be provided with means to release the blade from the guard when the handle is attached to the blade. In one form, the projection or finger on the handle can have a profile such that when it attaches to the blade, it also releases the blade from the guard thereby allowing the guard to be retracted to expose the blade.

The handle is provided with guide means to engage with the guard and to allow the guard to slide between retracted and extended positions. The guide means can be in the form of a recess in the handle in which the guide slides.

The guard can be retracted from the blade to expose various lengths of the blade. For instance, means may be provided to allow the guard to be releasably locked or held in various retracted positions to expose various lengths of the blade. This allows the cutting depth of the blade to be adjusted, and can also ensure that only a necessary amount of blade is exposed with the remainder of the blade still being protected by the guard, the purpose being to further minimise accidental injury.

BRIEF DESCRIPTION OF THE DRAWINGS

Embodiments of the invention will be described with reference to the following figures in which FIG. 1 is an exploded view of a known scalpel showing the scalpel blade, the blade guard, and the scalpel handle.

FIG. 2 shows the known scalpel blade assembly with the blade initially held within the guard.

FIG. 3 shows the known blade attached to the handle with the guard in the retracted position exposing the blade.

FIG. 4 is an enlarged view of the known blade guard illustrated in FIG. 1.

FIGS. 6A-6B illustrates a known blade guard.

FIGS. 7A-7G illustrates a known guard according to a second embodiment.

FIG. 16. Illustrates a further improvement which comprises a handle provided with engagement means to prevent the guard from being lifted out of the recess in the handle.

FIG. 17. Illustrates the handle of FIG. 16 with the guard attached.

FIG. 18. Illustrates a section view of the guard.

FIG. 19. Illustrates a section view of the handle in the recessed area of the handle.

FIG. 20. Illustrates a front view of the guard according to this improvement.

FIG. 21. Illustrates a rear view of the guard of FIG. 20

FIG. 22. Illustrates the front portion of the scalpel showing an engagement means to prevent over retraction of the guard according to a further improvement.

FIG. 23. Illustrates the scalpel of FIG. 22 with the guard next to the scalpel.

FIG. 24. Illustrates the scalpel of FIG. 23 in greater detail.

FIG. 25. Illustrates a side view of the scalpel containing the guard.

BEST MODE

Figure 5A:
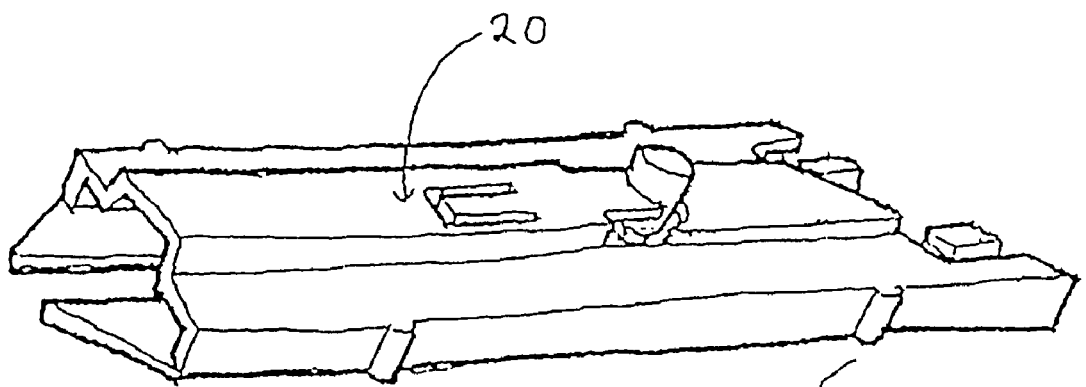
FIGS. 5A-5C show top, bottom and section views of a known blade guard according to an alternative embodiment.

Referring to FIGS. 1 and 7, there are illustrated two versions of a known scalpel which consist of three main components being a scalpel blade 10, a blade guard 11, and a scalpel handle 12. Blade 10 is of conventional design and is widely available in the marketplace. The blade is formed of stainless steel, has a forward cutting edge, and is provided with an elongate profile slot 13 which is again entirely conventional. Handle 12 has a forwardly extending projection or finger 14 which is profile and has opposed side recesses or grooves 15 (only one groove illustrated). Blade 10 is attached to finger 14 with the internal edges of slot 13 sliding along grooves 15. This is again conventional in the art.

FIG. 1 illustrates guard 11 which functions to cover or protect the cutting edge of blade 10 as the blade is attached. That is, blade 10 can be attached with guard 11 in place such that at no stage does a person's hand contact the cutting edge of the blade as the blade is attached to finger 14.

Figure 8:
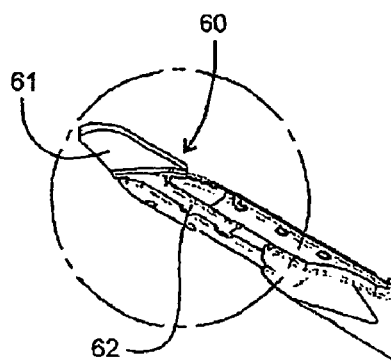
FIG. 8. Illustrates a scalpel having a blade assembly attached and showing a safety tab which comprises an improvement.

FIGS. 2 and 8 illustrate two versions of a scalpel blade assembly which consist of blade 10 and guard 11 with blade 10 now being entirely within guard 11. Guard 11 in FIGS. 2 and 8 is the same as guard 11 in FIGS. 1 and 7 except FIGS. 2 and 8 are inverted views of the guard of FIGS. 1 and 7.

Guard 11 can be formed from relatively inexpensive plastic material and is preferably clear or at least translucent such that that the blade can be seen through the guard. The guard substantially encompasses the blade to form a shroud or sleeve. The front 16 of the guard is open such that the guard can be retracted to expose blade 10. One side wall of guard 11 is provided with an elongate slot 17 which extends entirely along the side wall from the front 16 to the rear wall 18 of the guard. The function of slot 17 is to not interfere with retraction of the guard when blade 10 is attached to finger 14.

Figure 5B:
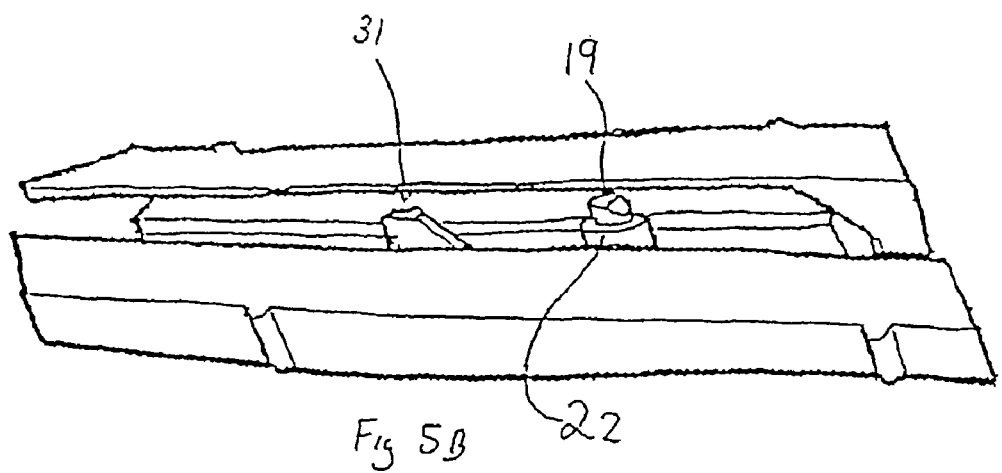
Figure 5C:
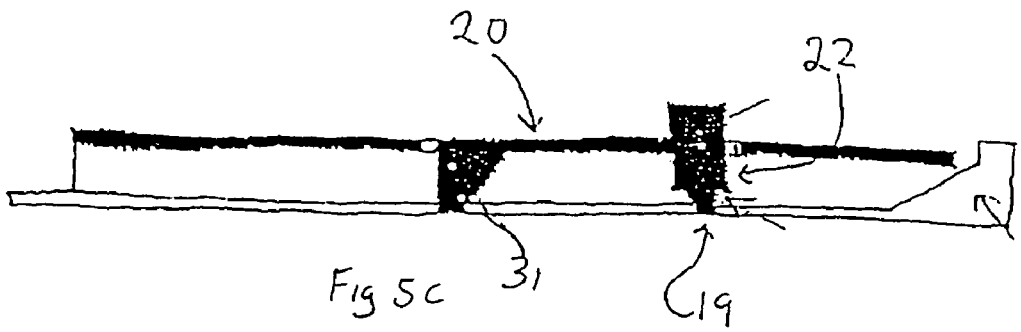
Figure 7C:
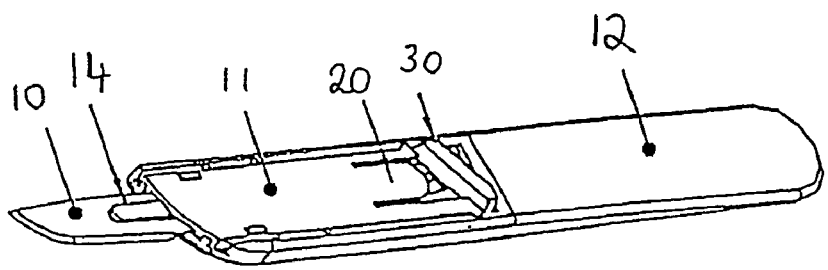
Figure 7D:
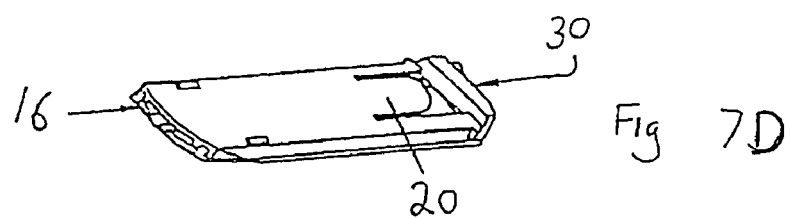
Figure 7E:
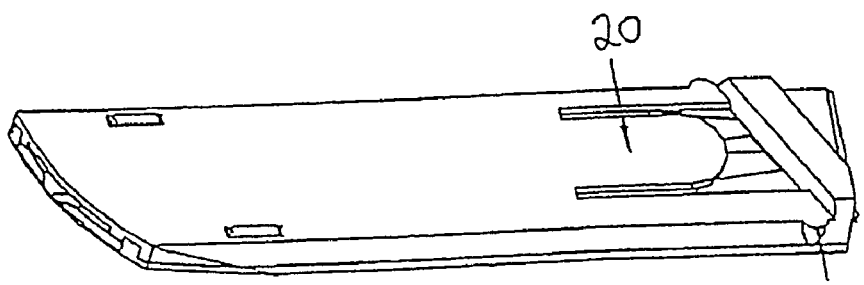
Figure 7F:
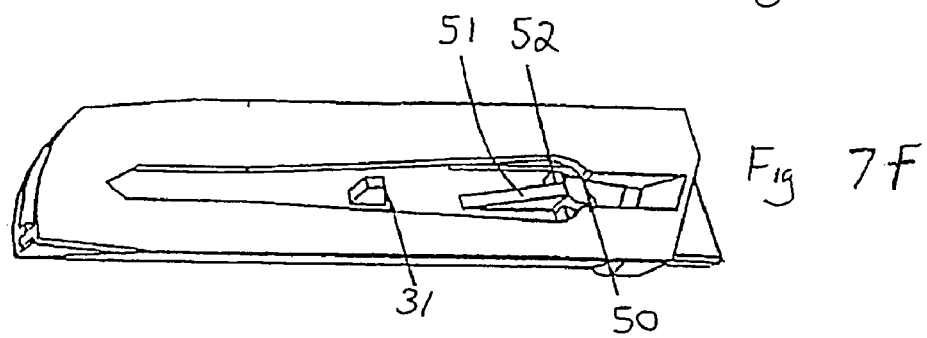
Figure 7G:
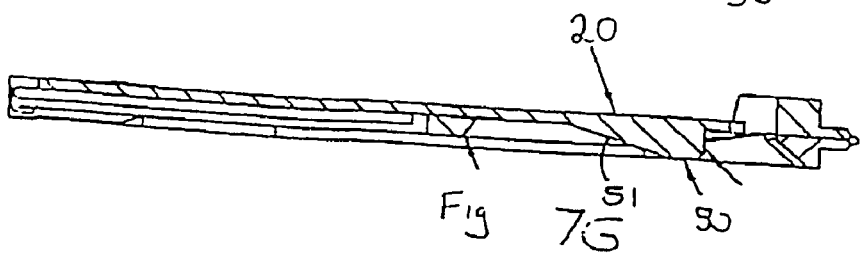
Figure 11:
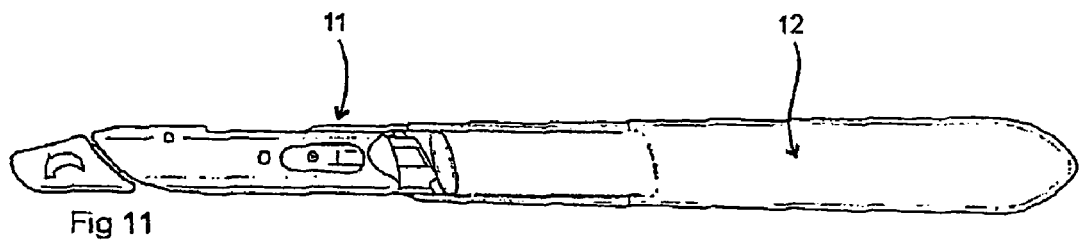
FIG. 11. Illustrates a side view of the scalpel of FIG. 8.
Figure 10:
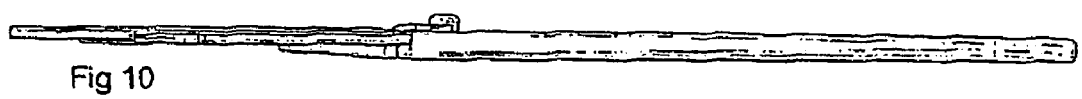
FIG. 10. Illustrates a top view of the scalpel of FIG. 8.

Guard 11 has a releasable attachment means which functions to hold blade 10 in guard 11 (see FIGS. 2 and 8) before the blade/guard assembly is attached to scalpel handle 12. In the embodiment of FIG. 2, the releasable attachment means is in the form of a projection or button 19 which is also illustrated in FIG. 5C. Button 19 sits at one end of a flat finger 20 (see FIG. 1). Finger 20 is integrally formed with the remainder of guard 11 and is able to be depressed by virtue of its finger-like quality.

A protective raised wall 21 extends around finger 20 but finger 20 is not attached to wall 21 which means that finger 20 can pivot or be depressed within the confines of wall 21. Wall 21 functions inter alia to protect the rather small finger against unintentional movement, or damage.

In the embodiment of FIGS. 7 and 8, the raised wall is not present. The projection 50 (see also FIG. 12) has a ramped wall 51 extending from finger 20.

In use, the scalpel blade assembly as illustrated in FIGS. 2 and 8 is assembled and can be placed in a foil package in a manner similar to current scalpel blades. The assembly can be removed from a foil package and it can be seen from FIGS. 2 and 8 that button 19,50 holds the blade within guard 11 and therefore the assembly can be picked up by guard 11 which means that there is little or no likelihood of the blade causing a stick injury.

The assembly can then be placed onto finger 14 with finger 14 passing into slot 13 to attach the blade to finger 14. Finger 14 is profile such that when it extends into slot 13, it also pushes away button 19, 50 against the bias of finger 20. This in turn releases blade 1 0 from its housing 11. For as long as blade 1 0 is attached to finger 14, the profile of finger 14 keeps button 19,50 out of slot 13 and therefore prevents button 19,50 from reengaging with the blade. Upon removal of the blade and guard assembly, the guard is first pushed to the forward position where it covers the blade and then the blade is decoupled from finger 14. As soon as this occurs, button 19, 50 is released and with the bias of finger 20 will re-enter into slot 13 to again hold the blade within the guard. The blade and guard assembly can now be safely disposed of in a sharps bin with little or no likelihood of stick injury resulting.

Finger 20 is biased to bias button 19, 50 into slot 13. In FIG. 2, button 19 extends from a larger shoulder portion 22 (more clearly illustrated in FIGS. 5B and 5C). Shoulder portion 22 is too large to extend through slot 13 but instead abuts against one side of the blade. With the biasing action of finger 20, shoulder portion 22 functions to gently push the blade against one side wall of guard 11 and prevents the blade from rattling or from exhibiting unintentional movement. The position of button 19 is such that when blade 10 is within guard 11 (see FIG. 2), the button is adjacent the rearpportion of slot 13. This prevents the blade from further extension out of the guard.

Figure 13:
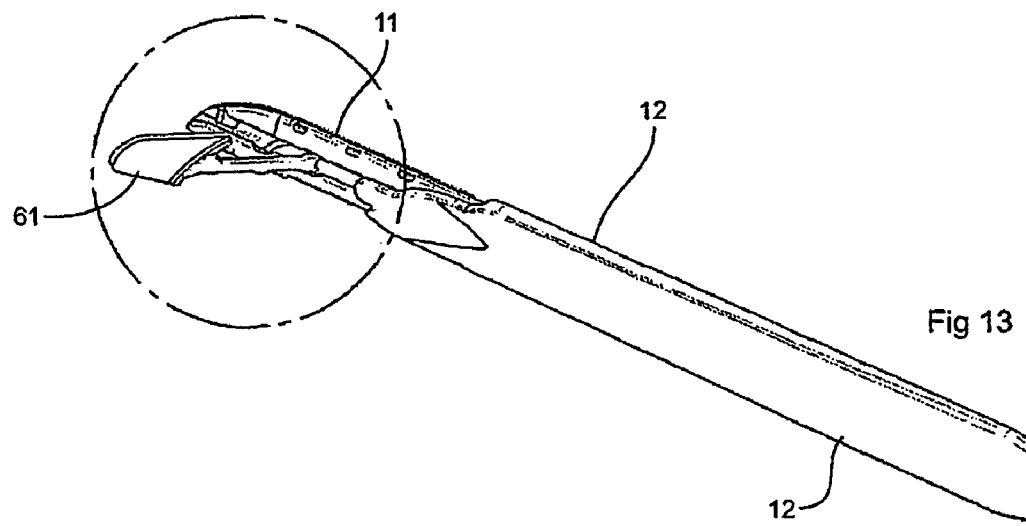
FIG. 13. Illustrates the safety tab being removed from the guard.
Figure 12:
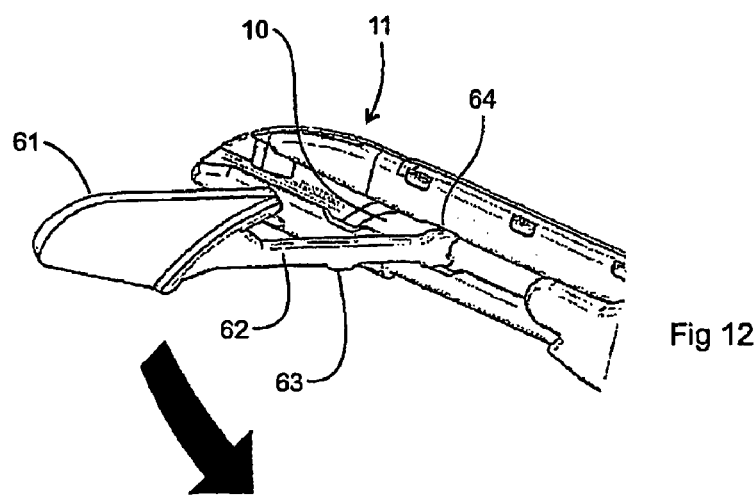
FIG. 12. Illustrates the safety tab being removed from the guard.

Movement of the blade in the other direction is prevented as rear end 18 of guard 11 does not have an open end as does the front 16. Thus, blade 10 is essentially trapped within housing 11 until such time as the assembly is attached to finger 14 which in turn pushes button 19 out of engagement with slot 13. In FIGS. 8, 12 and 13, button 50 has opposed shoulder portions 52 which serve the same function as shoulder portion 22 in FIG. 2.

Figure 9:
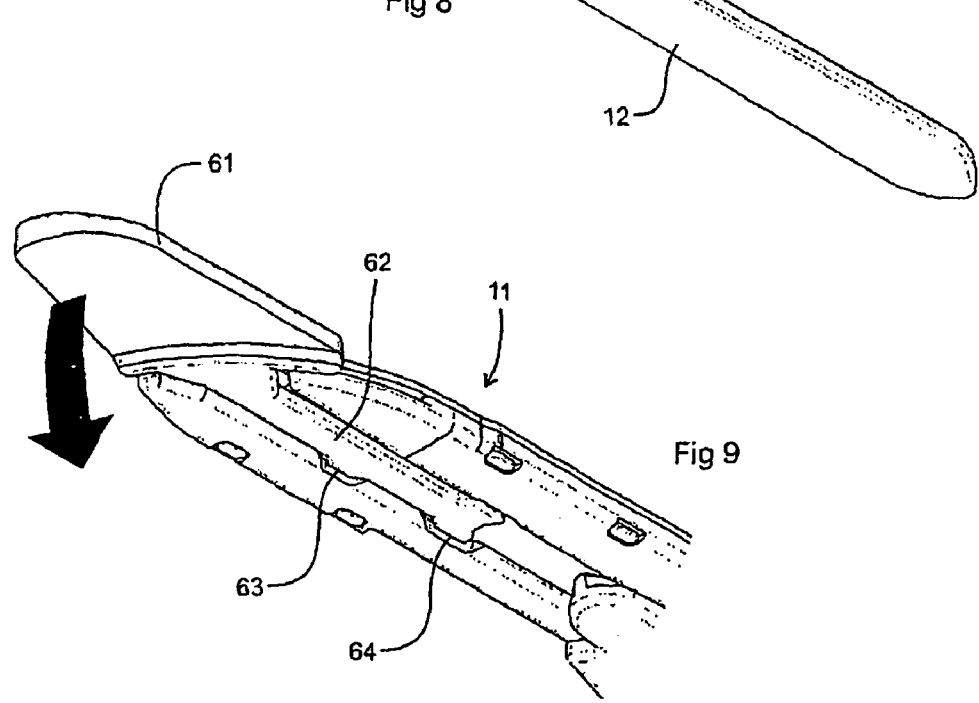
FIG. 9. Illustrates the safety tab in greater detail.
Figure 14:
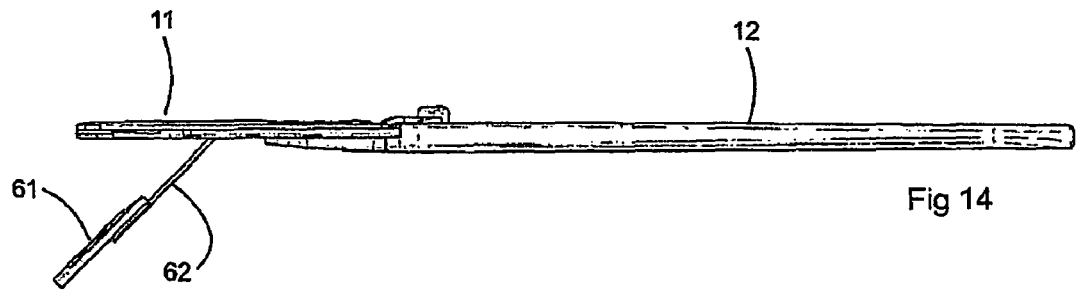
FIG. 14. Illustrates a top view of the scalpel having the safety tab being removed from the guard.

Handle 12 has a guide means 23 which in the embodiment is in the form of a recess 24 on the forward portion of handle 12 and immediately behind finger 14. The recess is sufficiently long such that guard 11 can be pulled back to fully expose blade 10. This fully retracted blade exposing position is illustrated in FIGS. 3 and 9. The recess 24, which forms part of the guide means in handle 12, is configured to accept the shape of guard 11.

Recess 24 has opposed side walls 25 which guide the opposed side walls 26 of guard 11.

Guard 11 has a number of small projections or buttons 27 extending from each side wall 26, and the side walls 25 of recess 24 have corresponding recesses 28. The function of buttons 27 and recesses 28 is to allow the guard 11 to be retracted along recess 24 and be releasably locked into preset positions where an opposed pair of buttons 27 click into an opposed pair of recesses 28. The releasable locking arrangement is such that the surgeon's thumb is able to slide the guard to release the guard from engagement with the guide means. However, when the surgeon's thumb is not on guard 11, the guard is held in place sufficiently to prevent it from inadvertently becoming loose. This arrangement has the advantage that if only a small part of the cutting blade is required, the guard can be clicked into an only partially retracted position thereby still protecting the remainder of the cutting edge of the blade against stick injury. The guard can also provide a means to measure the depth of the cut by exposing only a certain length of the cutting blade.

The guard has a thumb engageable projection 30 such that a surgeon can grip the guard by projection 30 and can extend or retract the guard in a single simple motion. Raised wall 21 prevents the surgeon's thumb from accidentally pushing in finger 20.

FIGS. 5A-5C and FIGS. 11-13 show variations to the guard.

In these variations, the guard has an additional fin 31 which sits in slot 13 of blade 10 and functions to keep the blade central. Fin 31 is also attached to finger 20 such that it is pushed out of the way when the blade is attached to the scalpel handle.

FIGS. 6A and 6B illustrate a blade guard 35 which is injection moulded and consists of two halves 36, 37 connected via a hinge line 38. The guard is moulded in a flat configuration illustrated in FIG. 6A. The blade 39 (see FIG. 6B) is placed on one half 37 and the other half 36 is bent via hinge line 38 to overlie the first half 37. The halves are snap locked together by projections 40 on one of the halves which engage into recesses 41 on the other half.

Referring now to FIGS. 8-15 there is illustrated a first improvement to the known type of scalpel blade assembly described above. This first improvement is directed to an improvement to the method of attachment of the blade assembly to the handle with reduced likelihood of a sharps incident. In the particular embodiment the improvement comprises a removable tab 60 which comprises a head portion 61 and a tail portion 62. Head portion 61 comprises a flat member which can be gripped between a person's fingers or which can be pushed against a hard surface. A downwardly extending lip 61a is formed at the rear of head portion 61. One end of tail portion 62 is integrally formed with head portion 61 and is positioned to at least partially fill slot 17 in guard 11. The slot 17 is illustrated in FIG. 2. The other end of tail portion 62 is joined to the lower end of lip 61a as shown in FIGS. 9, 12 and 13.

Tail portion 62 is attached to the remainder of guard 11 by a plurality of breakaway portions. In the particular embodiment, two sets of breakaway portions are provided which comprise a first breakable portion (a first neck 63), and a second breakable portion (a second neck 64). Each breakable portion comprises a pair of thin portions which can be torn away.

Referring to FIG. 12, the first neck 63 comprises a very thin portion which can be immediately broken away. Second neck 64 comprises thicker portions which are not as easily broken away. Thus, initial lifting of head portion 61 will break neck 63 to allow head portion 61 to be quite easily moved away from the rest of guard 11. After that, the tab must be twisted and pulled harder against the underside of blade 10 to allow neck 63 to be broken thereby allowing the tab to be removed entirely from guard 11. This ensures that the tab head 61 has moved sufficiently below with the line of the blade exposure to allow it to be safely operated by hand. Further pulling of the tab rearwardly will result in guard 11 being retracted to expose blade 10. Thus, the guard can be initially retracted as the safety tab is removed.

Figure 15:
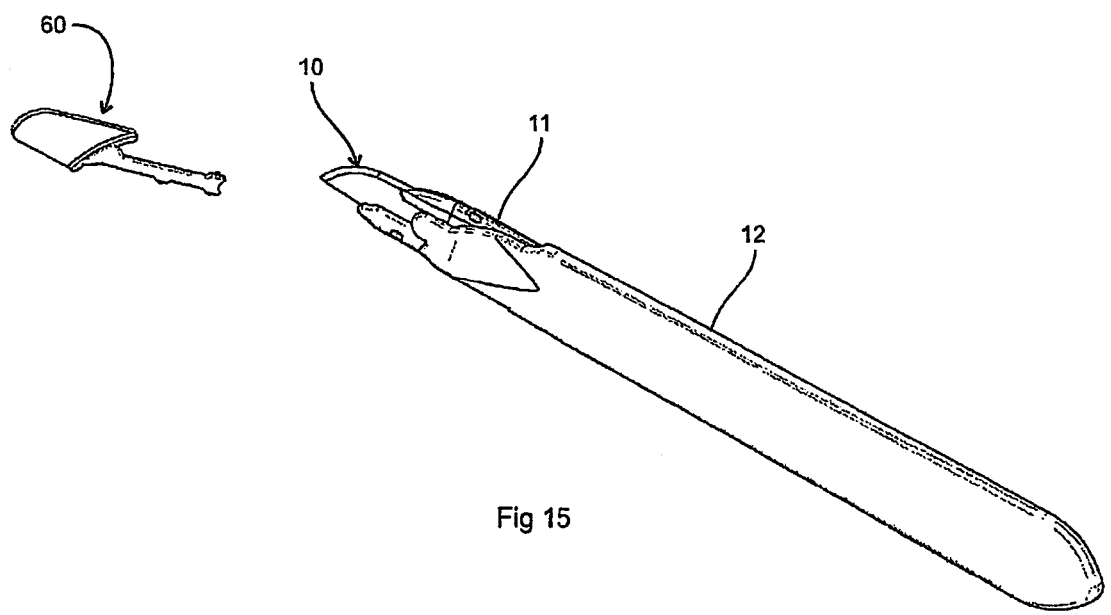
FIG. 15. Illustrates the safety tab completely removed.
Figure 26:
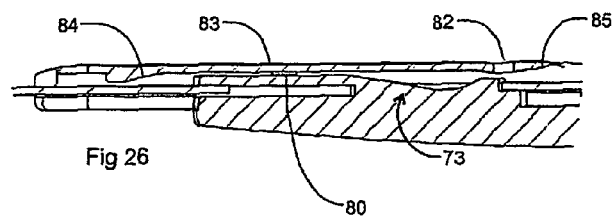
FIG. 26. Illustrates a section view of the front part of a scalpel according to another improvement which is directed to allowing the guard to "click" into the forward position and the rear position.
Figure 27:
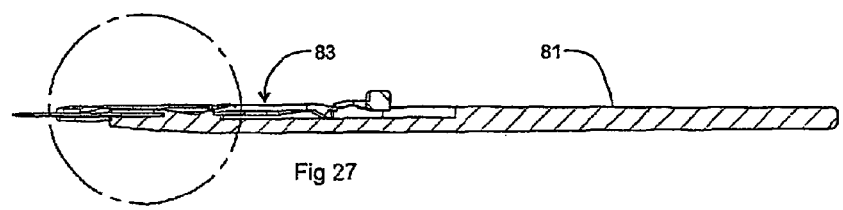
FIG. 27. Illustrates a top view of the scalpel of FIG. 26.
Figure 28:
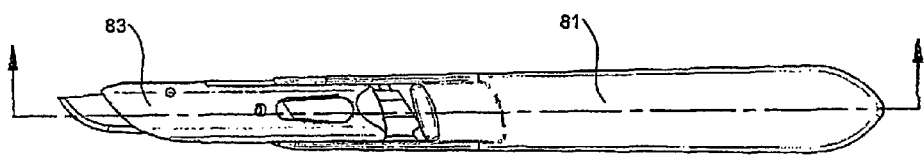
FIG. 28. Illustrates a side view of the scalpel of FIG. 26.
Figure 29:
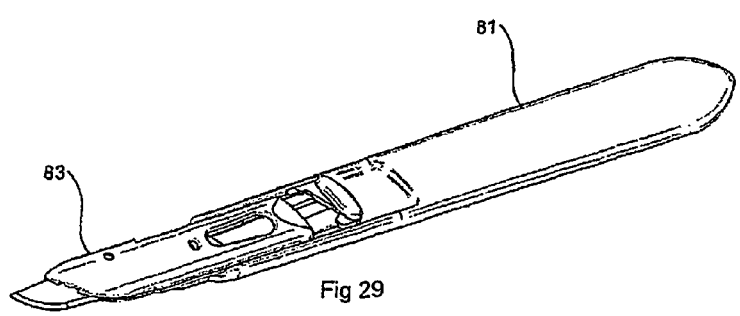
FIG. 29. Illustrates a perspective view of the scalpel of FIG. 26.

FIG. 15 shows the tab 60 completely removed from guard 11 and shows how guard 11 has been partially retracted to expose blade 10 in a very safe manner.

Another improvement to the scalpel is illustrated in FIGS. 16-21. Briefly, this improvement prevents the guard from lifting out of the handle. The improvement requires modification to the guard and modification to the handle. Referring to FIGS. 16-21, there is illustrated a modified handle 65. Handle 65 is provided with a recess 66. The recess has a side wall 67. Side wall 67 is provided with a longitudinal rib 68 which is best illustrated in the section view of FIG. 19. Guard 69 is similar to the guard described above except that one edge wall 70 of the guard 69 is provided with a longitudinal recess 71 which is best illustrated in the section view of FIG. 18. Thus, guard 69 is firmly held in recess 66 by having rib 68 trapped inside recess 71. This means that the guard 69 cannot be inadvertently lifted out of the recess 66 in handle 65.

FIGS. 22-25 illustrate another way to prevent the guard from being removed from the handle. Again, this improvement requires modification to the guard and to the handle. Guard 72 (see FIG. 23) is provided with an engagement means in the form of the safety catch which prevents guard 72 from being retracted too far rearwardly and thus possibly able to be retracted out of the recess 74 in handle 73. Specifically, the front of guard 72 is provided with a peg 75 best illustrated in FIG. 24. Peg 75 is formed integrally with guard 72 and extends at right angles from the front end of guard 72 such that peg 75 points towards handle 73 (in use). Peg 75 will abut against a stop 76 formed in handle 73 when guard 72 is fully retracted. Thus, guard 72 cannot be retracted too far as peg 75 will prevent this from occurring.

FIGS. 26-29 illustrate another improvement which is to provide a positive temporary locking of the guard when in the forward and the retracted position. In the embodiment, the arrangement is such to provide an audible "click" sound in the forward position and the retracted position such that the surgeon can be more confident of the guard being fully retracted or extended.

In the embodiment, this is achieved by providing at least one projection which can releasably engage with at least one recess when the guard is in the forward position and the retracted position. Specifically, the projection (locking bump 80) is provided of the handle 81 and the recess (location hole 82 is provided on guard 83. A ramp 84 is provided adjacent a forward part of the scalpel to lift the guard out of locking bump 80 as the guard is being retracted. Similarly, a ramp 85 is provided to lifted guard out of locking bump 80 when the guard is being extended.

Figure 30:
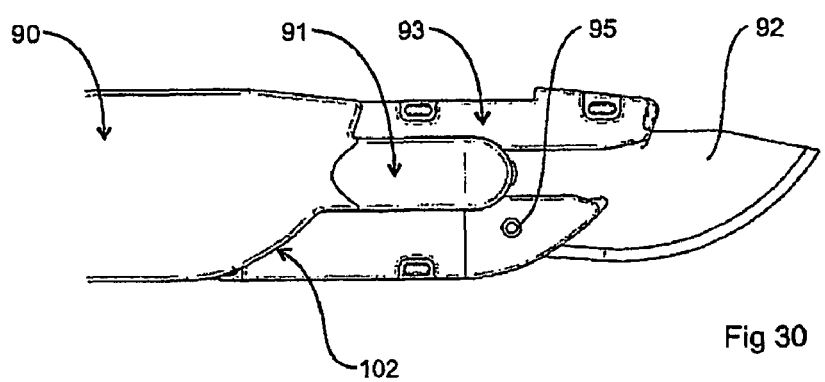
FIG. 30. Illustrates a modified guard attached to a handle.
Figure 31:
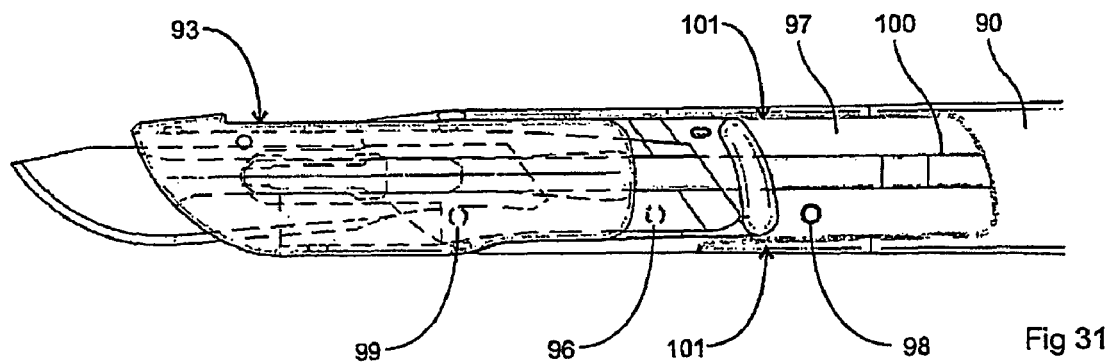
FIG. 31. Illustrates the guard of FIG. 30 from the other side.

Referring to FIGS. 30 and 31, there is illustrated a variation to the scalpel. The scalpel has a handle 90 containing a forwardly extending finger or nose portion 91 to which the scalpel blade is attached. The scalpel blade 92 is protected by the guard 93, the guard being substantially as described above. The scalpel blade 92 and guard 93 are attached to the forwardly extending finger 91 in the manner described above. This particular variation allows the guard 93 to be fully retracted and fully extended and provides an audible "click" when the guard is in the fully retracted position and the extended position. This allows the surgeon to retract the guard until the audible click is heard. When the guard is "clicked" into the retracted position, there is little likelihood of the guard being inadvertently moved to the forward position for the reasons described below.

Guard 93 is made of clear plastic material and contains a small extending button or projection 95 which is illustrated in FIG. 30. The button or projection is formed integrally with the guard 93 and is cylindrical having a diameter of approximately 1 mm and projecting (away from blade 92) by distance of about 1 mm. This button can be called the front button.

Guard 93 is also provided with a rear button 96 which has a size and shape similar to that of the front button 95, and rear button 96 is illustrated in FIG. 31.

The handle 90 is formed of plastic material and contains a recess 97 to accommodate guard 93 as guard 93 is retracted to expose blade 92. Recess 97 is formed with a rear hole 98 and a front hole 99 (both illustrated in FIG. 31). Each hole 98, 99 is designed to accommodate the respective front button 95 and rear button 96. Specifically, rear hole 98 accommodates rear button 96 and front hole 99 accommodates front button 95. As a button overlies a hole, the button is pressed into the hole and gives an audible "click" sound. Specifically, as guard 93 is retracted to expose blade 92, in the fully retracted position, the front button 95 passes into the front hole 99 at the same time that the rear button 96 passes into rear hole 98.

As guard 93 is retracted to expose blade 92, front button 95 at some stage will strike the front wall portion 102 of handle 90 (see FIG. 30). At this stage, the guard is sufficiently retracted to expose blade 92. A surgeon can either elect to keep the guard retracted in this manner and can easily push the guard back over the front of blade 92 to protect the blade when not required. However, when in this retracted position, the surgeon can also pull the guard back to a greater extent which will cause front button 95 to ride over front wall portion 102 and into engagement with front hole 99. In this fully retracted position, the guard is not easily (and therefore cannot inadvertently) move back to the blade protecting position.

Recess 97 contains a central elongate rib 100 and the rear of guard 93 is provided with a channel to enable the guard to slide along rib 100. The sidewalls 101 of recess 97 also guide the guard into a smooth retracting direction.

Figure 32:
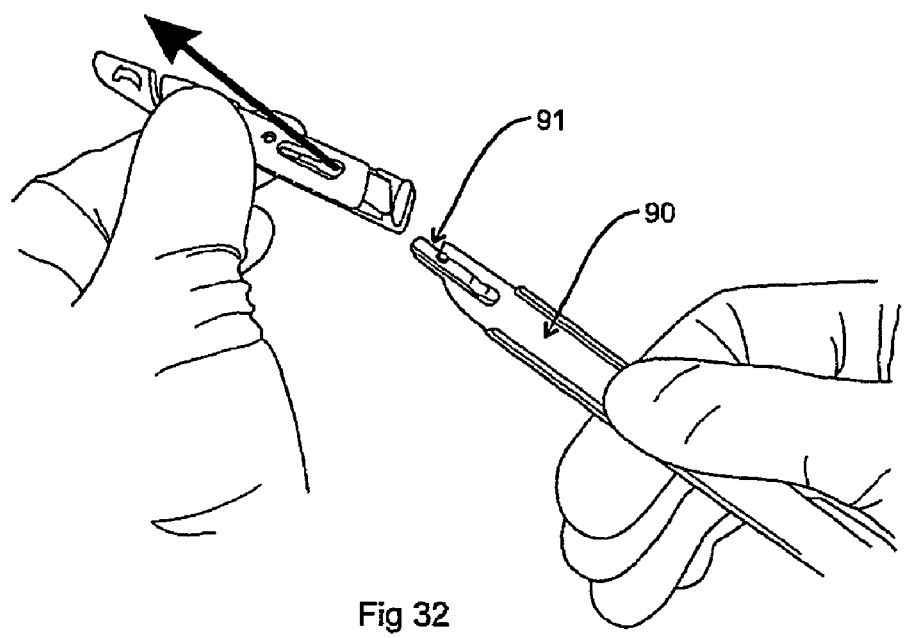
FIGS. 32-37 Illustrate the attachment and removal of the retractable guard assembly to a scalpel handle.
Figure 33:
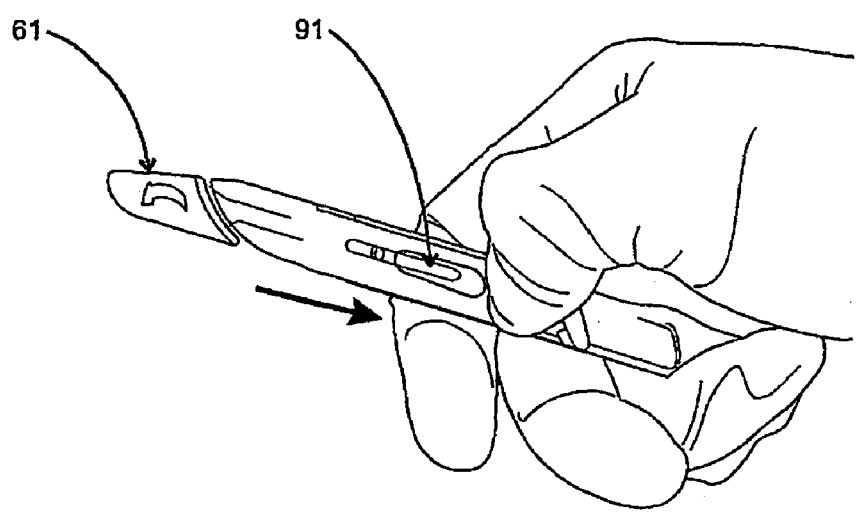
Figure 34:
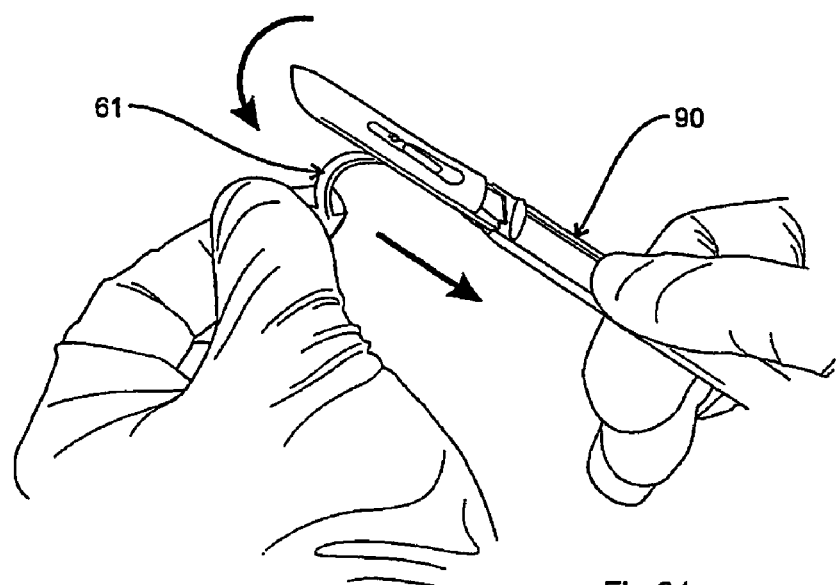
Figure 35:
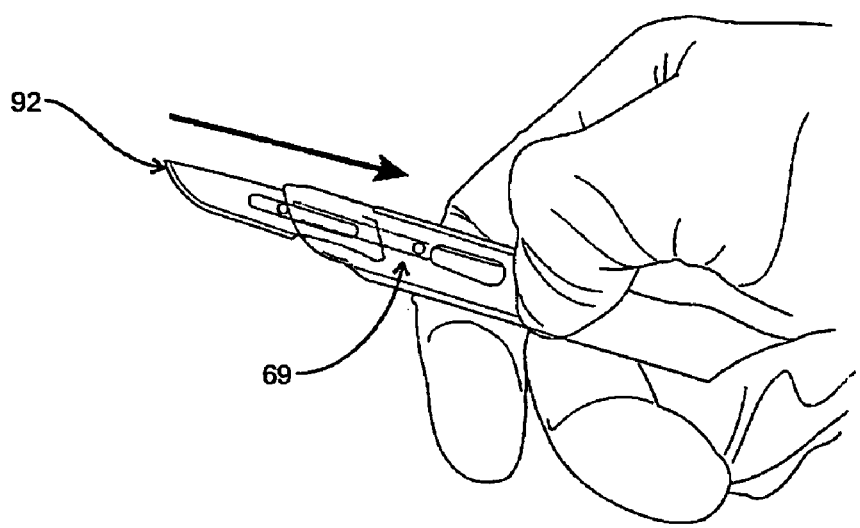
Figure 36:
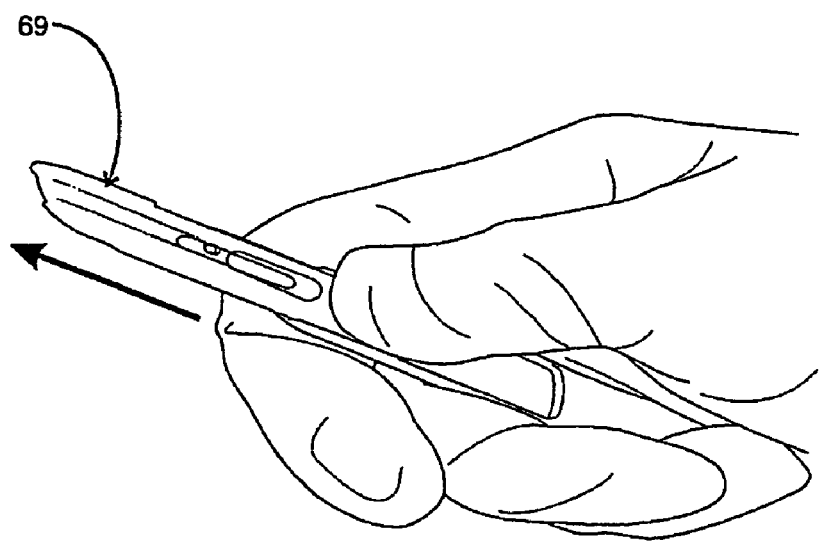
Figure 37:
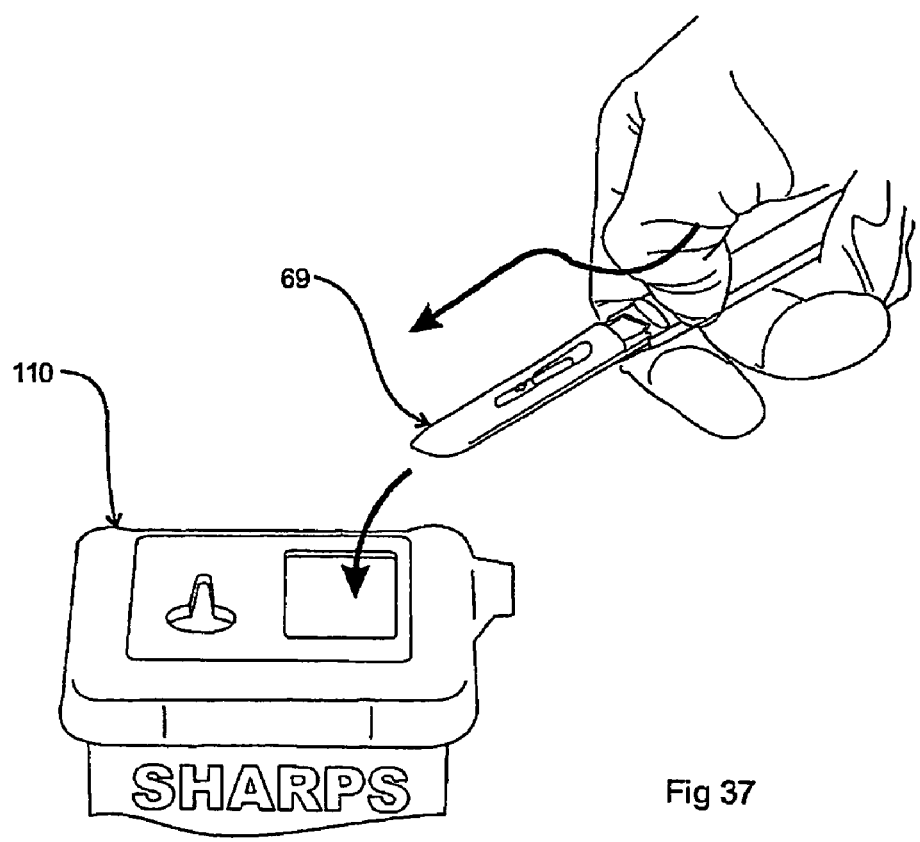

FIGS. 30 to 37 illustrate the attachment and removal of the protected scalpel blade to the handle. In FIG. 32, the blade 92 is mounted onto the handle by inserting the handle tip (finger) 91 into the blade slot as described above. The arrangement is then pulled back onto the handle until an audible click is heard when the arrangement is pulled back onto the handle to a sufficient amount. At this stage, the blade is not yet exposed. The safety tab 61 (see FIG. 33 and 34) is bent back and broken off. Only when the safety tab has been removed is the guard 69 pulled back (see FIG. 35) to expose blade 92. Typically, the person attaching the blade will have a "dominant" hand and a "free" hand. The guard is first attached to the handle using both hands (see FIG. 32). The dominant hand holds the handle and the free hand must be removed from the vicinity of the blade to prevent being cut. The safety tab 61 is designed to force the free hand to grip and remove the tab to prevent the free hand from manipulating the guard, and also ensures that the free hand is moved away from the blade by the downward motion of the free hand when tab 61 is removed (see FIG. 34) Guard 69 can be pulled back until an audible "click" is heard which means that the guard has been fully retracted to expose the blade. The guard can be pushed forwardly (see FIG. 36) to cover blade 92 and this can be done repeatedly especially when the scalpel is passed from one person to another person. To dispose of the blade and guard, the guard is pushed forwardly and is gently scooped to remove the blade from the handle. The blade containing the guard (the blade being covered by the guard and therefore preventing a sharps hazard) can then be discarded into a sharps container 110 (see FIG. 37).

It should be appreciated that various other changes and modifications can be made to the embodiment described without departing from the spirit and scope of the invention as claimed.

The invention claimed is:

1. A safety scalpel blade assembly adapted for attachment to a handle of the type which has a blade carrier in the form of a finger, the assembly comprising a scalpel blade which can be of conventional manufacture, the scalpel blade having a slot to allow the blade to be attached to the blade carrier on the handle, and a guard which extends at least about the cutting edge of the blade, the guard having attachment means to lock the blade to the guard as the assembly is being attached to the handle and which releases the blade from the guard when the blade is attached to the blade carrier on the handle, and a removable tab on the guard having a portion which can be gripped by a person, a slot formed in said guard, said removable tab comprising a head portion, a tail portion, and a lip defined between said head portion and said tail portion, the head portion of said tab extending forwardly of the blade assembly, the tail portion extending rearwardly at least partially into the slot in said guard, and the lip extending downwardly from said head portion to prevent the cutting edge of said blade from becoming exposed prior to removal of the tab, said head portion of said tab being gripped by a person to remove said head and free said tail portion from the slot in the guard to expose the cutting edge of said blade.

2. The assembly as claimed in claim 1, wherein the removable tab is attached to the guard via at least one breakable portion.

3. The assembly as claimed in claim 2, wherein the breakable portion comprises a first breakable portion (a first neck) and a second breakable portion (a second neck).

4. The assembly as claimed in claim 3, wherein the first breakable portion is closer to the head portion of the removable tab and breaks more easily than the second breakable portion.

5. The assembly as claimed in claim 1, comprising anti-lift means to reduce the ability of the blade guard from lifting relative to the handle.

6. The assembly as claimed in claim 5, wherein the anti-lift means comprises an engagement means on the handle which engages the guard.

7. The assembly as claimed in claim 6, wherein the engagement means comprises an elongated rib or rail in the handle, and a corresponding groove or slot in the guard (or vice versa) such that the guard can slide between the forward and the retracted position but is held against being lifted by the engagement of the rib or rail in the groove or slot.

8. The assembly as claimed in claim 1, comprising a safety catch to prevent excessive retraction of the guard, the safety catch being positioned on a forward part of the guard and comprising a projection.

9. The assembly as claimed in claim 1, comprising a location means to positively locate the guard in the extended position and the retracted position.

10. The assembly as claimed in claim 9, wherein the location means comprises at least one projection which releasably engages in at least one recess when the guard is in the extended position and the retracted position.

11. A safety scalpel assembly comprising a scalpel blade and a guard, the assembly being attachable to a handle of the type which has a blade carrier in the form of a finger, the scalpel blade having a slot to allow the blade to be attached to the blade carrier on the handle, and the guard extending at least about the cutting edge of the blade, the guard having attachment means to lock the blade to the guard as the assembly is being attached to the handle and which releases the blade from the guard when the blade is attached to the blade carrier on the handle, the guard moveable relative to the blade between an extended position, wherein the guard extends about the cutting edge of the blade, and a retracted position, wherein the blade is exposed, and anti-lift means to reduce the guard from lifting relative to the handle when the guard is moved between the extended and retracted positions, the anti-lift means comprising an elongate recess in the guard and a rib located within a recess on one side of the handle, the rib extending along the longitudinal axis of the handle and in line with the finger, the rib extending through the elongate recess in the guard upon retraction and extension of the guard.

12. The safety scalpel assembly of claim 11, further characterized by a safety catch to prevent excessive retraction of the guard, the safety catch being positioned on a forward part of the guard and comprising a peg extending outwardly from one side of the guard and able to engage with part of the handle to prevent excessive retraction of the guard.

13. The safety scalpel assembly of claim 11, further characterized by a location means, the location means comprising a projection on the guard which extends inwardly such that retraction of the guard causes the projection to ride over part of the blade and part of the finger and then to snap behind part of the handle when the guard has been fully retracted, and providing an audible click sound when the projection snaps behind part of the handle.

14. A safety scalpel comprising a handle of the type which has a blade carrier in the form of a finger, a scalpel blade which can be of conventional manufacture and which has a slot such that the scalpel blade is attached to the blade carrier of the handle, and a guard which extends about the cutting edge of the blade when the guard is in the extended position, and which exposes the blade when the guard is in the retracted position, the handle having a recess on one side of the handle, the invention being characterized by an anti-lift means comprising a longitudinal rib located within the recess that is in line with the finger, the guard containing a longitudinal recess, whereby upon retraction and extension of the guard, the longitudinal rib extends through the longitudinal recess of the guard.

* * * * *